US008021353B2

(12) United States Patent
Andersen et al.

(10) Patent No.: US 8,021,353 B2
(45) Date of Patent: Sep. 20, 2011

(54) HEAT EXCHANGER CONNECTOR ASSEMBLY

(75) Inventors: Eric Andersen, Braintree, MA (US);
David Baker, Greene, RI (US); Gregory Hughes, Hanover, MA (US); Liam O'Shea, East Greenwich, RI (US); Gary Searle, Norfolk, MA (US)

(73) Assignee: Smiths Medical ASD, Inc., Rockland, MA (US)

( * ) Notice: Subject to any disclaimer, the term of this patent is extended or adjusted under 35 U.S.C. 154(b) by 347 days.

(21) Appl. No.: 12/382,454

(22) Filed: Mar. 17, 2009
(Under 37 CFR 1.47)

(65) Prior Publication Data
US 2010/0241073 A1    Sep. 23, 2010

(51) Int. Cl.
*A61M 25/16* (2006.01)
*A61M 25/18* (2006.01)
*A61M 39/00* (2006.01)
*A61M 39/10* (2006.01)
*A61M 3/02* (2006.01)
*A61M 3/00* (2006.01)
*A61M 37/00* (2006.01)
*A61F 7/12* (2006.01)
*F04B 43/08* (2006.01)
*F04B 43/12* (2006.01)
*F04B 43/06* (2006.01)

(52) U.S. Cl. ............ 604/533; 604/39; 604/43; 604/113; 604/6.13; 604/905; 417/477.1

(58) Field of Classification Search .......... 604/113–114, 604/6.13, 95.05, 291, 533, 905, 910, 174, 604/30–43; 417/477.1–477.2, 477.9–477.12; 165/172–176
See application file for complete search history.

(56) References Cited

U.S. PATENT DOCUMENTS
4,568,255 A * 2/1986 Lavender et al. .......... 417/477.8
4,985,033 A * 1/1991 Boebel et al. ................. 606/148
(Continued)

FOREIGN PATENT DOCUMENTS
JP        04-306492        10/1992
(Continued)

OTHER PUBLICATIONS
PCT International Search Report and Written Opinion, ISA/KR, Oct. 20, 2010.

*Primary Examiner* — Nicholas D Lucchesi
*Assistant Examiner* — Rebecca E Eisenberg
(74) *Attorney, Agent, or Firm* — Louis Woo (57) ABSTRACT

A connector assembly for a heat exchanger has a fitting and a mount to which the fitting couples. The fitting has an elongate body having a proximal portion and a distal portion. At the proximal portion there is a crossbar, and at the distal portion there are an inlet and an outlet that protrude away from the body. Two wings extend from the body in a direction opposite to that of the inlet and outlet. There is formed on each of the wings a locking protrusion. The mount has a top portion where there is a groove dimensioned to accept the crossbar of the fitting. A longitudinal channel is formed orthogonal to the groove in the mount. Two sidewalls extend from the mount each for accepting a corresponding one of the wings, when the fitting is coupled to the mount. Apertures are provided at the sidewalls at the wings.

24 Claims, 8 Drawing Sheets

U.S. PATENT DOCUMENTS

| | | | | |
|---|---|---|---|---|
| 5,255,676 A | * | 10/1993 | Russo | 128/207.14 |
| 6,047,699 A | * | 4/2000 | Ryatt et al. | 128/207.17 |
| 2008/0140054 A1 | * | 6/2008 | Lee | 604/533 |
| 2008/0208208 A1 | * | 8/2008 | Nagata et al. | 606/108 |
| 2009/0205814 A1 | | 8/2009 | Kume | |

FOREIGN PATENT DOCUMENTS

| | | |
|---|---|---|
| JP | 05-149691 | 6/1993 |
| JP | 10-122786 | 5/1998 |
| JP | 2007-333373 | 12/2007 |
| KR | 10-2005-0004657 | 1/2005 |

* cited by examiner

HEAT EXCHANGER CONNECTOR ASSEMBLY

FIELD OF THE INVENTION

The present invention relates to heat exchangers, and more particularly to a connector assembly that connects a heat exchanger to a heater so that a heated fluid from the heater may be sent to the heat exchanger for warming an infusate or a physiological fluid flowing therethrough.

BACKGROUND OF THE INVENTION

Heat exchangers for warming physiological solutions are known. Some of the connector assemblies used for coupling a heat exchanger to a heater are disclosed in U.S. Pat. Nos. 4,878,537, 5,097,898, 5,417,274 and RE39,075, all of which are assigned to the assignee of the instant invention. As disclosed, the user has to carefully snap-fit the connector fitting of the heat exchanger to the interface input and output ports of the heater. This oftentimes requires that the user has to carefully guide the heat exchanger to the heater mount, and from there to the mount interface.

SUMMARY OF THE PRESENT INVENTION

The connector assembly of the instant invention provides an easier and more accurate mating of the heat exchanger connector fitting to the heater.

The connector assembly of the instant invention moreover is adapted to be used with different kinds of heat exchangers, including the triple lumen heat exchanger disclosed in the aforenoted '898 patent, the disclosure of which is incorporated by reference herein.

The present invention connector assembly is moreover usable with the heat exchanger disclosed in co-pending application entitled "Multi-Lumen Heat Exchanger" having attorney docket No. 0107/0059. The disclosure of the co-pending '059 application is incorporated by reference herein.

The heat exchanger connector assembly of the present invention has two main portions: a fitting to which the infusate line and the heat exchanger for heating the infusate flowing through the infusate line, and a mount at the heater to which the fitting is coupled so that the heated fluid from the heater may be input to the heat exchanger for heating the infusate or the physiological fluid passing through the heat exchanger. To that end, the fitting is designed to have an elongate body having a proximal portion to which two arms extend to form a cross bar. At a lower portion of the body there is provided an inlet and an outlet. Gaskets may be fitted to the inlet and the outlet to prevent fluid from being leaked therefrom. For easy handling, the fitting is also provided with a pair of wings that extend in a direction away from the protruding inlet and outlet, so that a user can grasp the wings to manipulate the fitting. At the proximal end of the fitting, there is a proximal port to which an infusate line may be connected to enable infusate to flow into the fitting. At the distal end of the fitting there is a distal port to which a heat exchanger is connected. The heat exchanger may be either that disclosed in the aforenoted '898 patent or that disclosed in the aforenoted '095 co-pending application. The fitting is configured to have its inlet and outlet connected to a corresponding lumen in the heat exchanger, and also allow the infusate line to be connected to an infusate lumen at the heat exchanger.

The second portion of the inventive connector assembly is a mount that is a part of a heater device. The mount has at its upper end a groove configured to accept the cross bar of the fitting. A central channel orthogonal to the groove is provided in the mount for accepting the elongate main body of the fitting. An input port and an output port are provided at the mount for mating with the outlet and the inlet, respectively, that protrude from the fitting. Two sidewalls extend from the mount to embrace the fitting, with each sidewall being positioned adjacent to a corresponding wing of the fitting, when the fitting is fully coupled to the mount. A base at the mount supports the lower edges of the wings of the fitting, while a cut out thereat allows the elongate body of the fitting to pass as it is being positioned in the channel.

To couple the fitting to the mount, a user places the crossbar of the fitting onto the groove formed at the mount orthogonal to the channel, while maintaining the body at an angle to the mount, so that a pivot is established by the crossbar resting in the groove. Once a pivot is established, the user pivotally moves the elongate body of the fitting towards the mount so that the elongate body is positioned in alignment with the channel of the mount. At which point the inlet and outlet of the fitting are mated to the output port and input port, respectively, formed at the mount. The gaskets fitted to the inlet and outlet of the fitting, once the fitting is securely coupled to the mount, prevent any leakage of fluid. Particular gaskets may be fitted to the inlet and outlet which would open only when the fluid circulating between the heater and the heat exchanger are flowing under pressure, as for example when the fluid is being circulated by a pump in the heater. Alternatively, the gaskets may be forced open and remained open were the output and input ports to have integral protrusion members that push open the gaskets when the inlet and outlet are mated to the output port and input port, respectively.

To securely retain the fitting to the mount, locking mechanisms are provided at each of the wings to coact with locking mechanisms provided at each of the sidewalls of the mount when the fitting is firmly coupled to the mount. These locking mechanisms, without any external removal forces applied to the wings of the fitting, would securely maintain the fitting to the mount.

To remove the fitting from the mount, a user grasps the wings and presses them towards each other to release the fitting from the mount. The removal of the fitting from the mount is done in the reverse fashion per above discussed, in that the user would pivot the elongate body of the fitting away from the mount, with the crossbar of the fitting resting in the groove of the mount acting as the pivot.

To ease the manufacturing process for the fitting of the heat exchanger connector assembly, a casing in the form of a cartridge that may be made from the same PVC material as the fitting is fitted over the inlet and outlet of the fitting, so as to eliminate the need to solvent bond the valve gaskets individually to the inlet and outlet of the fitting. The casing is made to have two bores or passages, one for the inlet and the other for the outlet. Valve gaskets are assembled into the passages and the thus assembled casing is fitted to the fitting, with the valve gasket of respective ones of the passages assembled onto the corresponding inlet and outlet of the fitting, thereby providing sealing for the inlet and outlet of the fitting. Once assembled to the fitting, the casing is bonded to the fitting, by means of for example ultrasonic bonding or solvent bonding, so that the casing is fixedly retained to the fitting and in fact may be considered as a part of the fitting. The valve gaskets at the inlet and outlet are accordingly fixedly held to the inlet and outlet by the casing, so that when the fitting is removed from the mount, the valve gaskets will remain attached to the inlet and outlet of the fitting, thereby providing sealing both while the inlet and outlet are mated to the output and input ports, respectively, of the mount, and after the fitting has been removed and the flaps of the valve gaskets returned to the their original positions to prevent leakage of fluid from the fitting.

The present invention is therefore directed to a connector assembly that comprises: a fitting having a body including a proximal portion and a distal portion, with two arms forming a crossbar provided at the proximal portion, an inlet and an outlet protruding from the distal portion, and two wings extending in a direction opposite the direction to which the inlet and the outlet protrude; and a mount to which the fitting couples that has a longitudinal channel for accepting the body of the fitting, a groove orthogonal to the channel onto which the crossbar of the fitting rests when the body is positioned in the channel, and an input port and an output port for mating with the outlet and inlet, respectively, of the fitting when the body of the fitting is positioned in the channel.

The present invention also relates to a connector body that comprises a fitting connected to a heat exchanger having an elongate body, the body of the fitting having a crossbar provided at its proximal portion and an inlet and outlet protruding from its distal portion, with two wings extending in a direction opposite the direction to which the inlet and outlet protrude; and a mount to which the fitting couples having a longitudinal channel for accepting the body of the fitting, a groove orthogonal to the channel onto which the crossbar makes contact before the body is pivotally moved into position in the channel with the crossbar resting on the groove, and an inlet port and outlet port provided at the mount for mating with the outlet and inlet, respectively, of the fitting when the body is positioned in the channel.

The present invention is further directed to an apparatus that comprises: a fitting having an elongate body, the body having a crossbar provided at its proximal portion and an inlet and an outlet protruding from its distal portion; a mount to which the fitting couples having a longitudinal channel for accepting the body of the fitting, a groove orthogonal to the channel onto which the crossbar of the fitting makes contact before the body is pivoted into position with the channel with the crossbar resting on the groove, and an input port and output port for mating with the outlet and inlet, respectively, of the fitting when the body is positioned within the channel; a heat exchanger connected to a distal end of the fitting, the heat exchanger having a plurality of lumens one of which connected to an input and an other of which connected to the outlet, the one and other lumens fluidly connected at a distal end to establish a through fluid path therebetween; a heater to which the mount is a part of, the heater heating a fluid to a predetermined temperature, the heated fluid being output to the heat exchanger from the output port of the mount to the inlet of the fitting and flows from the one lumen to the other lumen and the outlet to be returned to the heater via the input port of the mount so that the return fluid is reheated by the heater to the predetermined temperature.

BRIEF DESCRIPTION OF THE FIGURES

The present invention will become more apparent and the invention itself will be best understood with reference to the following description of the invention taken in conjunction with the following drawings, wherein.

DETAILED DESCRIPTION OF THE INVENTION

Figure 1:
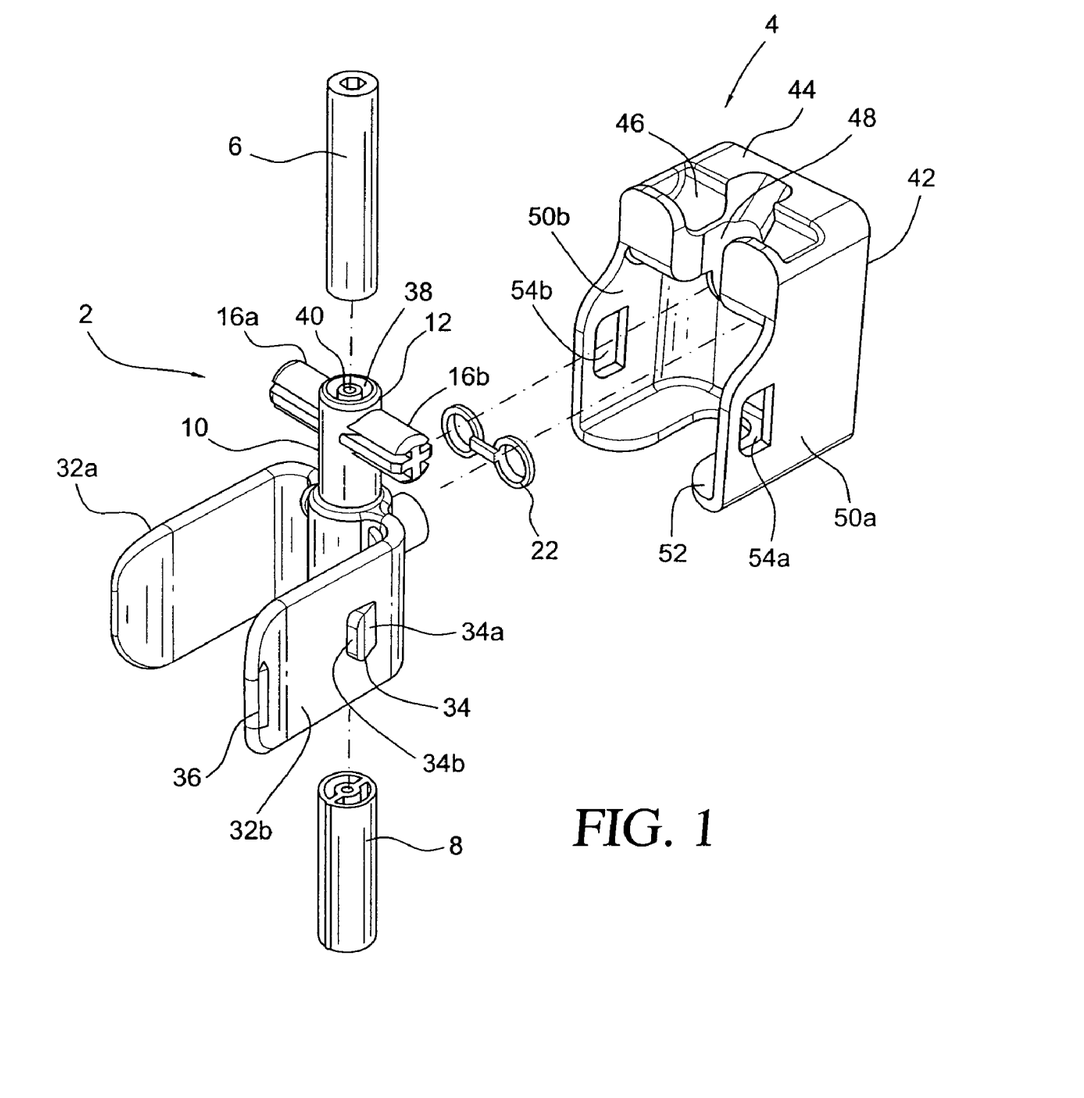
FIG. 1 is a disassembled view of the connector assembly of the instant invention.

With reference to FIG. 1, the present invention heat exchanger connector assembly is shown to include a fitting 2 and a mount 4 to which the fitting is to be coupled. Also shown are an infusate line 6 and a heat exchanger in the form of a multiple lumen tubing 8.

Figure 2:
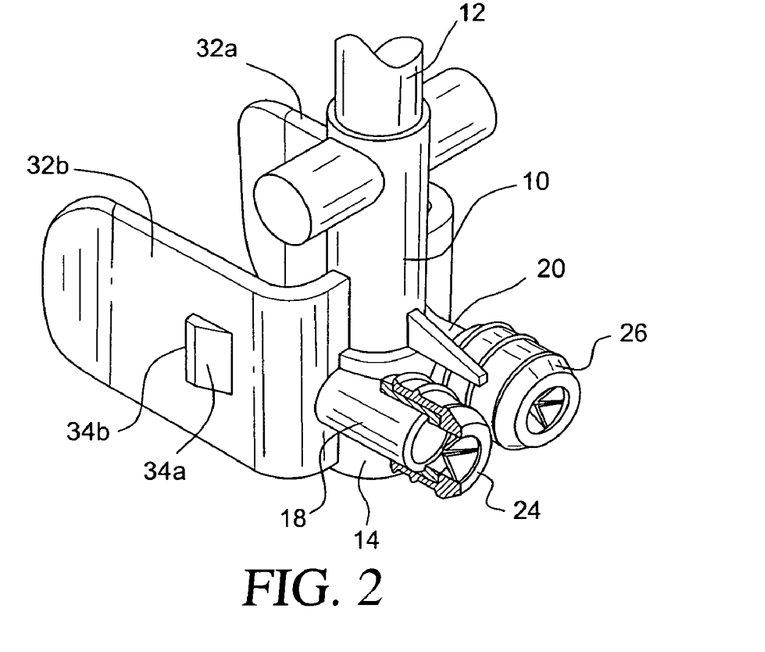
FIG. 2 is a perspective view of the fitting of the connector assembly showing the inlet and outlet fitted with rubber duckbill type cone gaskets.
Figure 3:
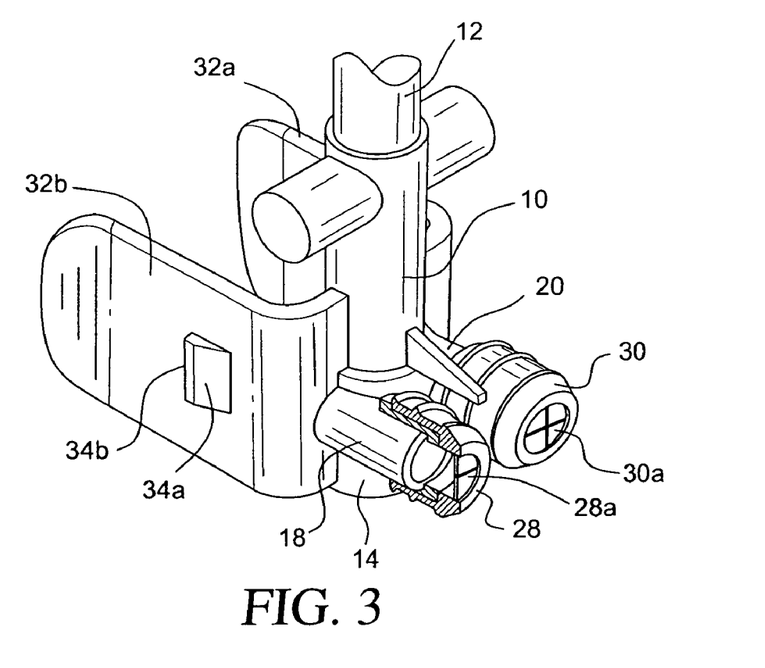
FIG. 3 is a perspective view of the fitting of the connector assembly of FIG. 1 showing the inlet and outlet fitted with respective rubber multi-flap type cone gaskets.

Fitting 2, which may also be referred to as a reflux connector in that it enables the circulation of a fluid into and out of the heat exchanger, is shown to include an elongate body 10 having a proximal portion 12 and distal portion 14, best shown in FIGS. 2 and 3. Extending in opposed direction from the distal portion 12 of body 10 are two arms 16a and 16b that together form a crossbar at the proximal portion of fitting 2.

With reference to FIGS. 2 and 3, an inlet 18 and an outlet 20 protrude from body 10 of the fitting. To prevent leaking when the inlet and outlet are mated to the mount, to be discussed in greater detail below, the inlet and outlet of the fitting may be fitted with a one-piece rubber or silicone gasket, such as 22 shown in FIG. 1. Alternatively, each of the inlet and outlet may be fitted with an individual cone rubber or silicone gasket that may have a duckbill type valve, such as gaskets 24 and 26 shown in FIG. 2, a multi-flap type valve such as gaskets 28 and 30 shown in FIG. 3, or a single slit valve such as gaskets 74 and 76 shown in FIG. 8. For gasket 24, the duckbill valve points inward towards the inlet, so that the valve would open when fluid is fed to the inlet under pressure, or if the valve flaps are pushed open by a protruding member that feeds the fluid to the inlet. Otherwise, valve 24 stays closed to prevent leaking. On the other hand, for gasket 26 fitted to outlet 20, the duckbill valve points away from the outlet, so that only when fluid from the outlet is to be output from the fitting would the valve open. Otherwise, the valve stays closed to prevent leaking as well as input of fluid to the fitting. The gaskets may be made from a medical grade elastomer or silicone material, including for example Santoprene.

FIG. 3 shows the multi-flap type rubber gasket that may be fitted to the inlet and outlet of fitting 2. The valves of gaskets 28 and 30 each have a plurality of flaps 28a and 30a, respectively, that stay substantially planar relative to the opening of the inlet/outlet, and would remain in the closed position unless the flaps are forced open in a given direction by the fluid flow under pressure. Also, the flaps may be forced open were the mount to which the inlet and outlet are to couple have integral cannulas that respectively mate with the inlet and outlet.

Fitting 2 further has a pair of wings 32a and 32b that are pointing in a direction opposite to the direction in which the inlet 18 and outlet 20 protrude from body 10 of fitting 2. Each of wings 32a and 32b has a locking mechanism 34 that has an incline 34a rising to a backstop 34b. Fitting 2 is made of a medical plastics material such as for example PVC, urethane or pebax, so that there is a given elasticity provided to wings 32a and 34b. Accordingly, wings 32a and 34b may be grasped by a user and squeezed towards each other. Indentations 36, shown in FIG. 1, may be provided at the end portions of the wings to allow the user to more readily grasp the wings, and therefore also be better able to maneuver fitting 2.

As best shown in FIG. 1, fitting 2 has a proximal port at its proximal end 12 to which infusate line 6 may be connected, so that infusate may flow into fitting 2. Also shown is a multiple lumen heat exchanger tubing 8 connected to a distal port, not shown, at distal portion 14 of fitting 4. The heat exchanger may be that disclosed in the aforenoted '749 patent, per shown in FIG. 1, or it may be the multi-lumen heat exchanger disclosed in the aforenoted and incorporated by reference '059 co-pending application.

Fitting 2 is configured such that its inlet and outlet are connected to respective one and other lumens in the heat exchanger. The inlet and outlet lumens are fluidly connected at the end of the heat exchanger distal from fitting 2, per described in the aforenoted '059 application, so that a fluid input to the inlet of fitting 2 will flow through the fitting to the inlet lumen of the heat exchanger and be returned by the outlet lumen of the heat exchanger to the outlet of the fitting.

Fitting 2 is moreover configured to have an infusate port, designated 40 in FIG. 1, that fluidly interconnects infusate line 6 to the infusate lumen of heat exchanger 8. As described in the co-pending '059 application, the infusate input to fitting 2 is passed therethrough to heat exchanger 8, and from there to a patient line for output to a patient.

Mount 4, which is attached to a heater or the heat exchanger, not shown, has a top portion 44 extending from a back wall 42 whereon a groove 46 is formed. Groove 46 lies orthogonally to a channel 48 having a dimension for accepting elongate body 10 of fitting 2. Mount 4 further has an input port and an output port, shown more clearly in the embodiment of FIGS. 4A and 4B, to which the outlet and inlet, respectively, of fitting 2 are mated when body 10 of the fitting is firmly coupled to channel 48, with arms 16a and 16b of the crossbar resting in groove 46 of mount 4.

There are two sidewalls 50a and 50b that extend from back wall 42 of mount 4. The sidewalls 50a and 50b are connected to a floor or base 52 that has an inwardly U-shaped cutout. The inwardly U-shaped cutout of base 52 allows mount 4 to accommodate heat exchanger 8 connected to the distal end of body 10, when fitting 2 is coupled to mount 4. The bottom edges of wings 32a and 32b rest on base 52 when fitting 2 is securely coupled to mount 4.

As shown, each of sidewalls 50a and 50b has a locking mechanism that correspondingly coacts with the inclined protrusion 34 at a corresponding one of wings 32 of fitting 2. For the exemplar mount shown in FIG. 1, these locking mechanisms are apertures 54a and 54b at sidewalls 50a and 50b, respectively.

Figures 6, 7A, 7B:
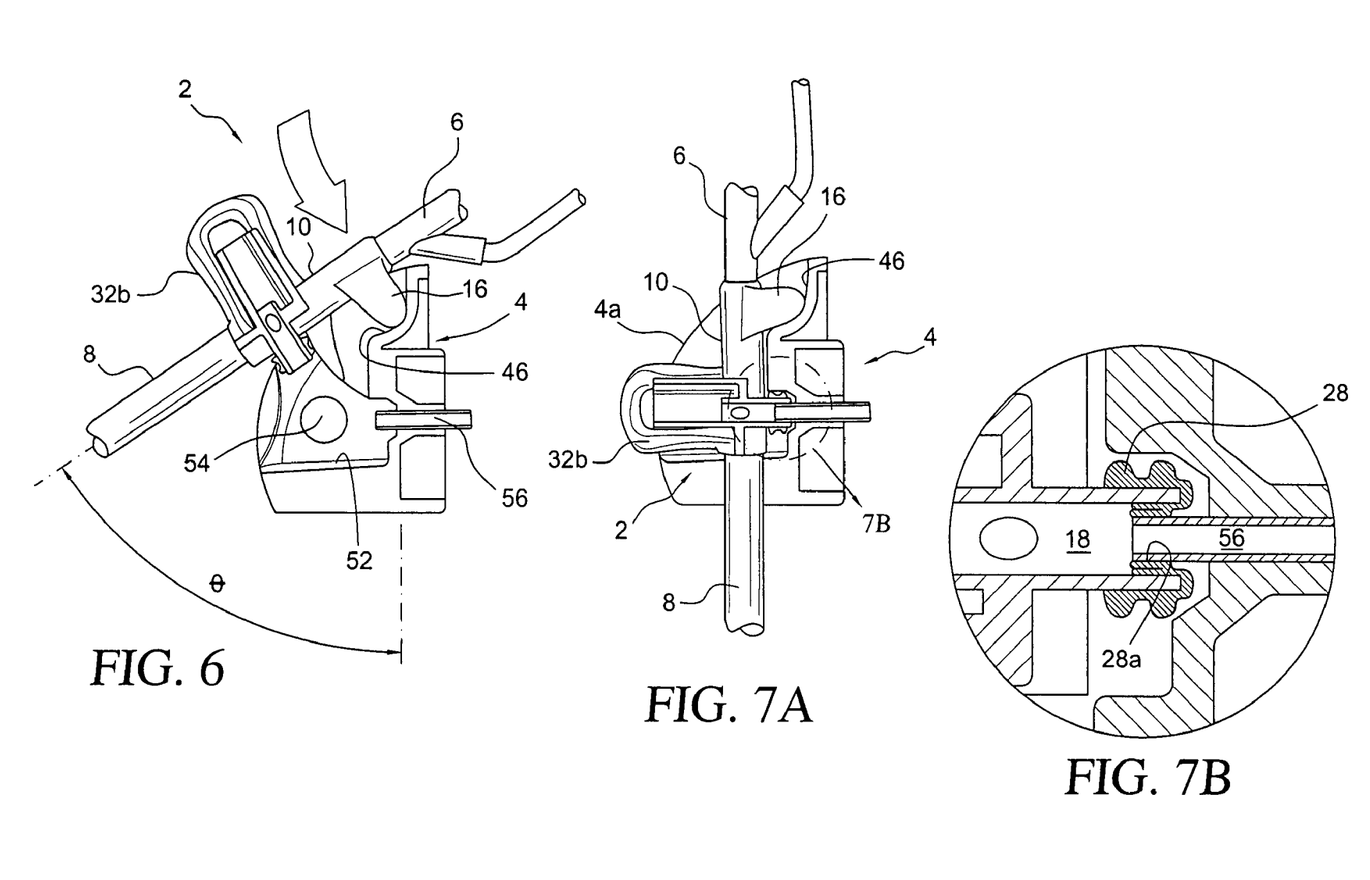
FIG. 6 is semi-cross-sectional view of the position of the inventive fitting relative to the inventive mount prior to the fitting being coupled to the mount.
FIG. 7A is a semi-cross-sectional view of the fitting coupled to the mount.
FIG. 7B is an enlarged semi-cross sectional view of the mating of the inlet (or outlet) of the fitting to the output port (or input port) of the mount.

In use, as illustrated in FIGS. 6, 7A and 7B of the to be discussed embodiment, fitting 2 is tilted at an angle θ relative to mount 4, with arms 16a and 16b making contact and resting in groove 46, so that a pivot point is provided for fitting 2 relative to mount 4. Once arms 16a and 16b are properly fitted within groove 46, elongate body 10 of fitting 2 may be pivotally moved into position per shown in FIG. 7A, so that its inlet 18 and outlet 20 are mated to the output port and input port, respectively, at mount 4. As body 10 is pivotally moved towards mount 4, given that wings 32a and 32b are made of plastics and therefore have a given flexibility, the inclined protrusions 34 at the wings would come into contact with sidewalls 50a and 50b, and be biased thereby until the respective apexes of protrusions 34 pass the sidewalls and enter apertures 54a and 54b. At which time wings 32a and 32b would return to their original positions, thereby securely retaining fitting 2 to mount 4.

To remove fitting 2 from mount 4, a user would grasp wings 32a and 32b and move those wings relatively towards each other so that protrusions 34 are disengaged from apertures 54a and 54b. At that point, a reverse pivotal movement may be effected on fitting 2 to remove it from mount 4. When fitting 2 is firmly seated to mount 4, with its inlet and outlet mated to the output port and input port, respectively, of the mount, arms 16a and 16b are firmly resting within groove 46. Added to that the bottom edges of wings 32a and 32b resting on base 52 means that fitting 2 is firmly coupled to mount 4, and is not removable therefrom, unless a user deliberately presses wings 32a and 32b towards each other to disengage the protrusions 34 from apertures 54a and 54b. The elastomeric gaskets 24 and 26 fitted to inlet 18 and outlet 20, respectively, ensure that there is no fluid leak between inlet 18 and the output port and outlet 20 and the input port of mount 4 while fitting 2 is coupled to mount 4. Gaskets 24 and 26 further ensure that there is no fluid leak at inlet 18 and outlet 20 when fitting 2 is disengaged from mount 4, as the gaskets 24 and 26 (more particularly their flaps) return to their natural position to retain the fluid in fitting 2, and therefore prevent the fluid in the disposable device connected thereto via infusate line 6 and multiple lumen tubing 8 from leaking out. The gasket fitted inlet and outlet therefore prevent fluid leaks and potential hazards that may result from such leaks. Whether or not fitting 2 is properly engaged to mount 4, or more particularly whether inlet 18 and outlet 20 are fully mated to the output port and input port, respectively, of the fluid heater may be detected by a sensor (not shown) provided at the heater relative to mount 4, similar to the detector mechanism in the HOTLINE fluid warmers being sold by the assignee of the instant invention.

Figures 4A, 4B, 5A, 5B:
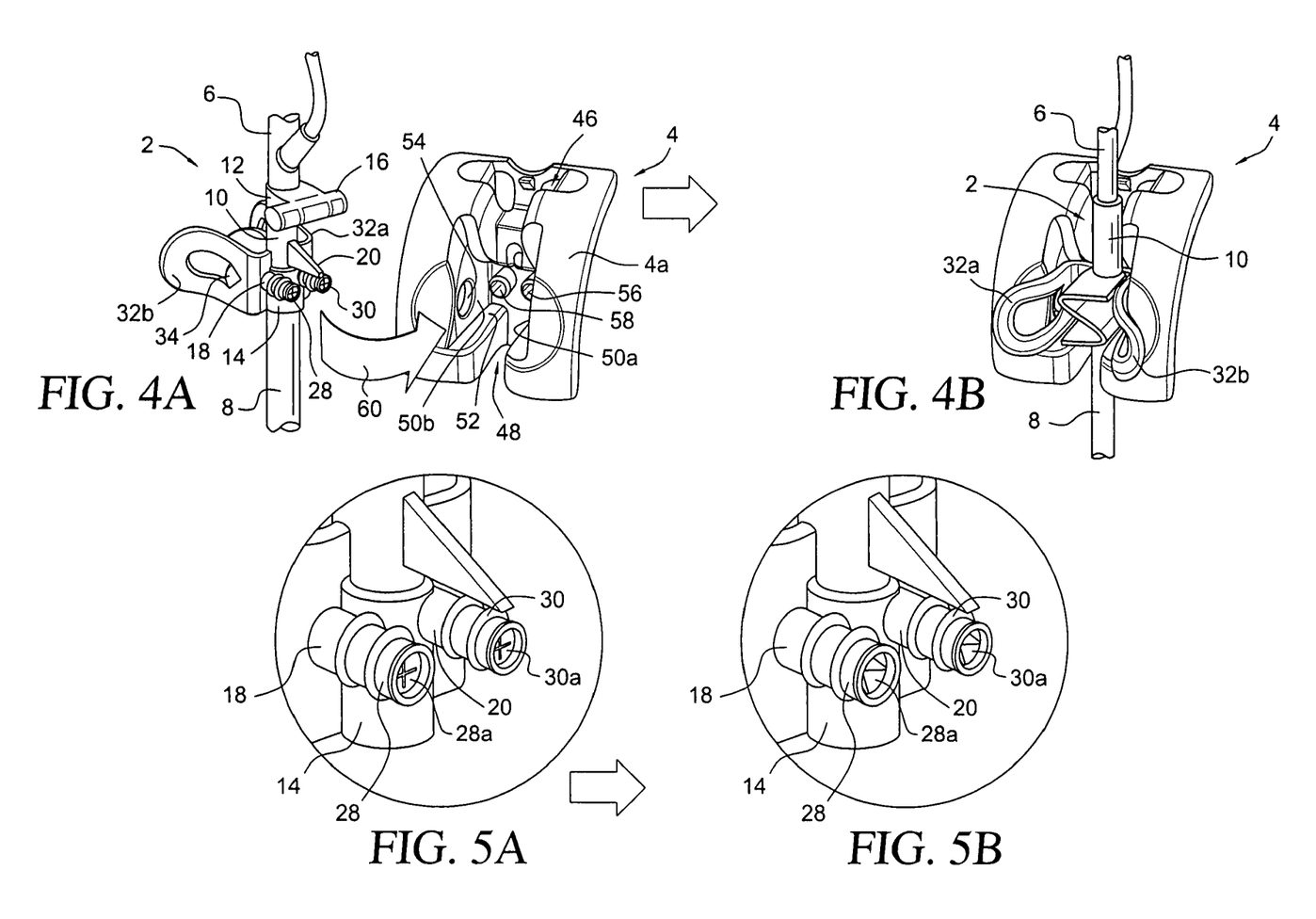
FIG. 4A shows another embodiment of the instant invention connector assembly with the fitting removed from the mount.
FIG. 4B shows the second embodiment of the inventive connector assembly with the fitting coupled to the mount.
FIG. 5A is an enlarged view of the inlet and outlet of the fitting fitted with multi-flap type cone gaskets.
FIG. 5B shows the operation of the valves of the cone gaskets.

FIGS. 4a and 4b illustrate a second embodiment of the connector assembly of the instant invention. Although it looks somewhat different from the earlier discussed embodiment of FIG. 1, this embodiment operates and functions the same as the FIG. 1 embodiment. Accordingly, those elements that are functionally the same as the elements described in the FIG. 1 embodiment are labeled the same.

Fitting 2 for the FIG. 4 embodiment also has an elongate body 10 with a proximal portion 12 where there is extended a crossbar. For this embodiment, the crossbar is designated 16, instead of arms 16a and 16b in the FIG. 1 embodiment, as the crossbar extends cantilever like from body 10. Body 10 also has a proximal portion 14 where an inlet 18 and an outlet 20 protrude along the same direction as crossbar 16. As shown, each of the inlet 18 and outlet 20 is fitted with a gasket, which likewise may be a rubber or silicone multi-flap cone gasket, such as 28 and 30 shown in the enlarged view of distal portion 14 in FIG. 5a. A cone type rubber gasket with the flaps in the shape of a duckbill valve such as that described in FIG. 2 may also be used.

Fitting 2 further has extending from body 10 in a direction opposite to that of inlet 18 and outlet 20 a pair of wings 32a and 32b. At each of the wings 32 there is a locking mechanism, in the form of a protrusion 34 (only protrusion 34 at wing 32b is shown). For the FIG. 4A embodiment, infusate line 6 and the heat exchanger 8 are shown to be connected to the corresponding port at the proximal end and the distal end, respectively, of fitting 2

Mount 4 for the FIG. 4A embodiment is shown to have a curved front surface 4a opening into a longitudinal channel 48. There is also provided orthogonal to channel 48 a horizontal groove 46 dimensioned to accept crossbar 16. At the back wall of mount 4 there are provided an output port 56 and an input port 58 that are matable with inlet 18 and outlet 30, respectively, of fitting 2. There are further two sidewalls 50a and 50b at mount 4. Each of the sidewalls is dimensioned to be adjacent to a corresponding one of wings 32a and 32b of fitting 2, when fitting 2 is coupled to mount 4. At each of the sidewalls 50a and 50b there is provided a second locking mechanism in the form of an aperture 54 (shown only on sidewall 50b) that coacts with protrusion 34 at a corresponding one of the wings. An inward U-shaped base 52 at mount 4 supports the bottom edge of each of wings 32a and 32b.

Fitting 2 is movable in the direction shown by directional arrow 60 so as to be coupled to mount 4, per shown in FIG. 4B. When fitting 2 is properly coupled to mount 4, its inlet 14 and outlet 20 are mated to output port 56 and input port 58, respectively, of mount 4. At the same time, the protrusion 34 at each of wings 32a and 32b engages apertures 54 of the sidewalls 50a and 50b, thereby securely retaining fitting 2 to mount 4.

FIG. 5A is an enlarged view of inlet 14 and outlet 20 of fitting 4 having fitted thereto rubber or silicone multi-flap cone gaskets 28 and 30. As shown in FIG. 5b, assuming that inlet 18 and outlet 20 are mated to the output port and input port, respectively, of mount 4 and that a heated fluid from the heater (not shown) is being circulated into fitting 2, note that the flaps 28a of the valve of gasket 28 are pointing inwards towards the inside of inlet 18 to allow fluid to pass into the fitting 2, whereas the flaps 30a of the valve at gasket 30 are pointing away from the outlet 20 so that the fluid inside the fitting is being returned to the input port of mount 4. Accordingly, the heated fluid from the heater is circulated through fitting 2, and of course through the above discussed lumens in heat exchanger 8 for warming the infusate being input from infusate line 6. A heater or heat exchanger to which mount 4 may be a part of may be the fast flow fluid warmer being sold by the assignee of the invention under the trade name Level 1® H-1200, or any of assignee's HOTLINE and other similar fluid warmers.

FIG. 6 shows the initial positioning of fitting 2 relative to mount 4. As shown, crossbar 16 rests on groove 46, with body 10 of fitting 2 being at an angle θ relative to mount 4. With cross bar 16 and groove 46 providing a pivot point, fitting 2 can readily and pivotally be moved into position relative to mount 4, per shown in FIG. 7A, with its inlet and outlet mated to the output port and inlet port, respectively, of mount 4. This is more clearly shown by the enlarged view of the semi-crossed sectional view of inlet 18 mated to the outlet port 56 of FIG. 7B. Thus mated, the flaps 28a and 30a of the gaskets 28 and 30, respectively, are pushed back, per shown in FIG. 7B with respect to flaps 28a, so that respective through fluid paths are established between output port 56 and inlet 18, and input port 58 and outlet 20.

To remove fitting 2 from mount 4, the reverse pivotal movement takes place, with the user first pressing wings 32a and 32b towards each other so that protrusion 34 at each of the wings disengages from aperture 54 at each of the sidewalls 50 of mount 4. Once body 10 of fitting 2 is decoupled from mount 4, crossbar 16 can be lift off of groove 46.

Figure 8:
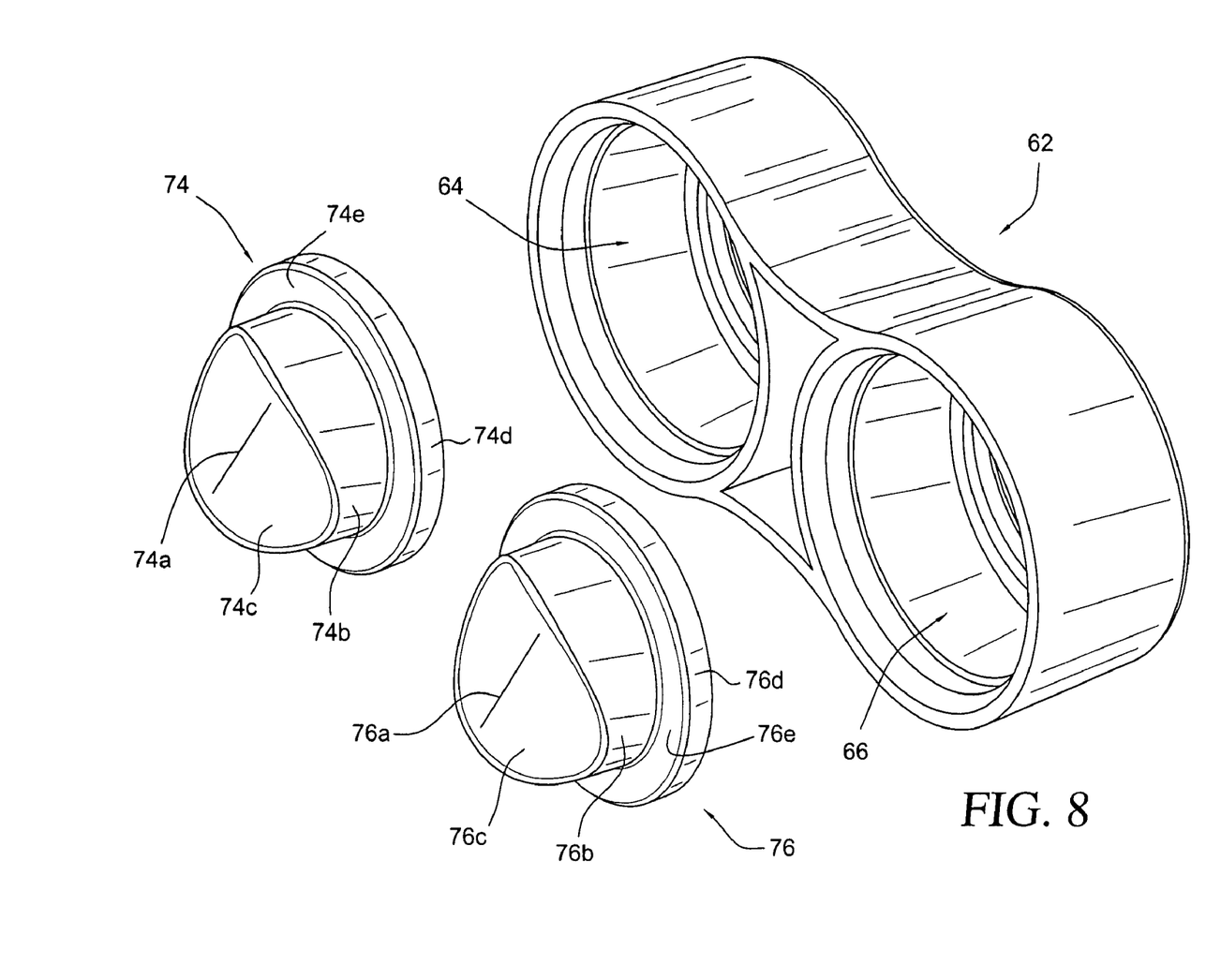
FIG. 8 is a perspective view showing a cartridge casing of the instant invention, and the valve gaskets that are to be assembled into the bore or passages of the casing.
Figure 9:
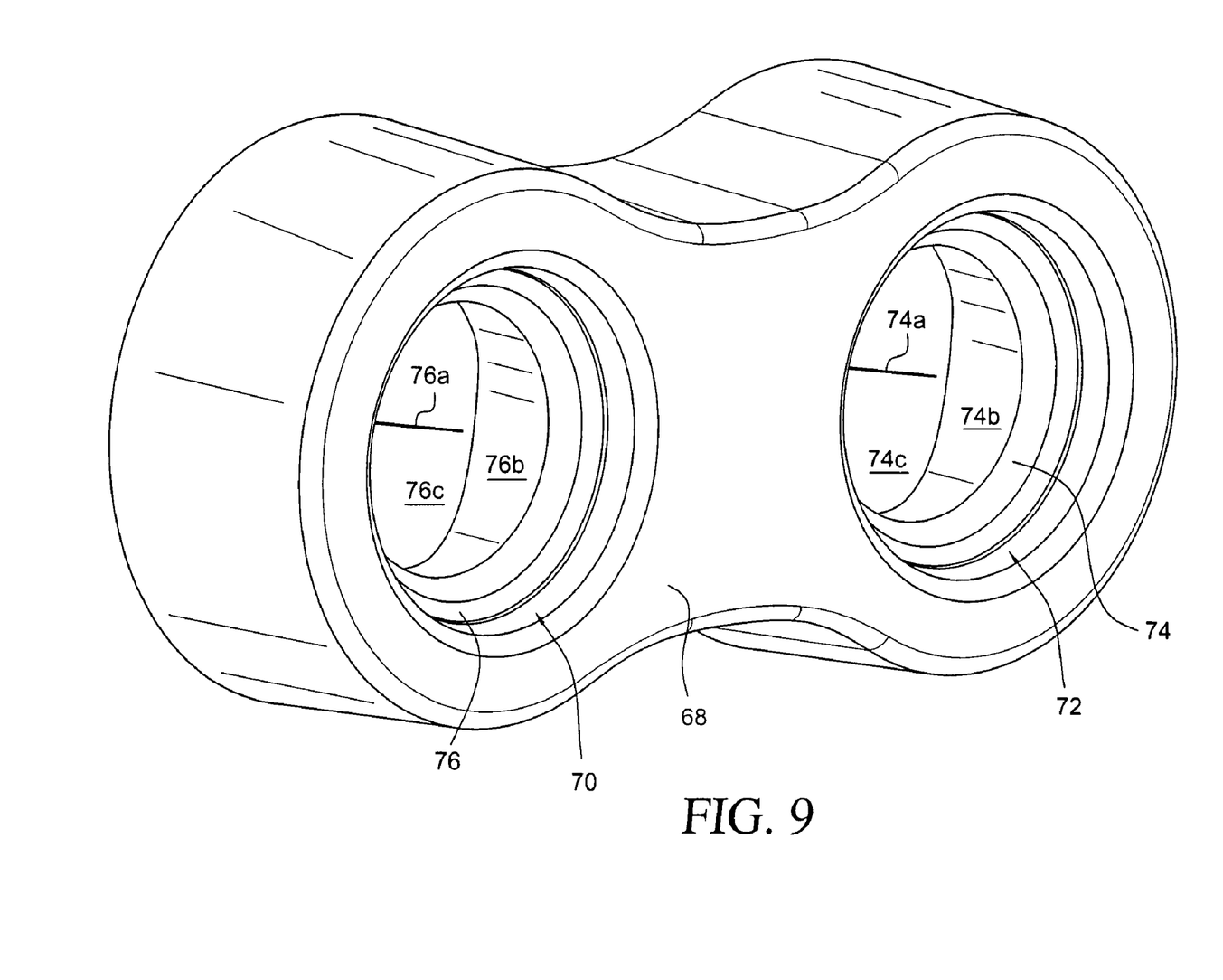
FIG. 9 shows a casing having assembled therein the valve gaskets.
Figure 10:
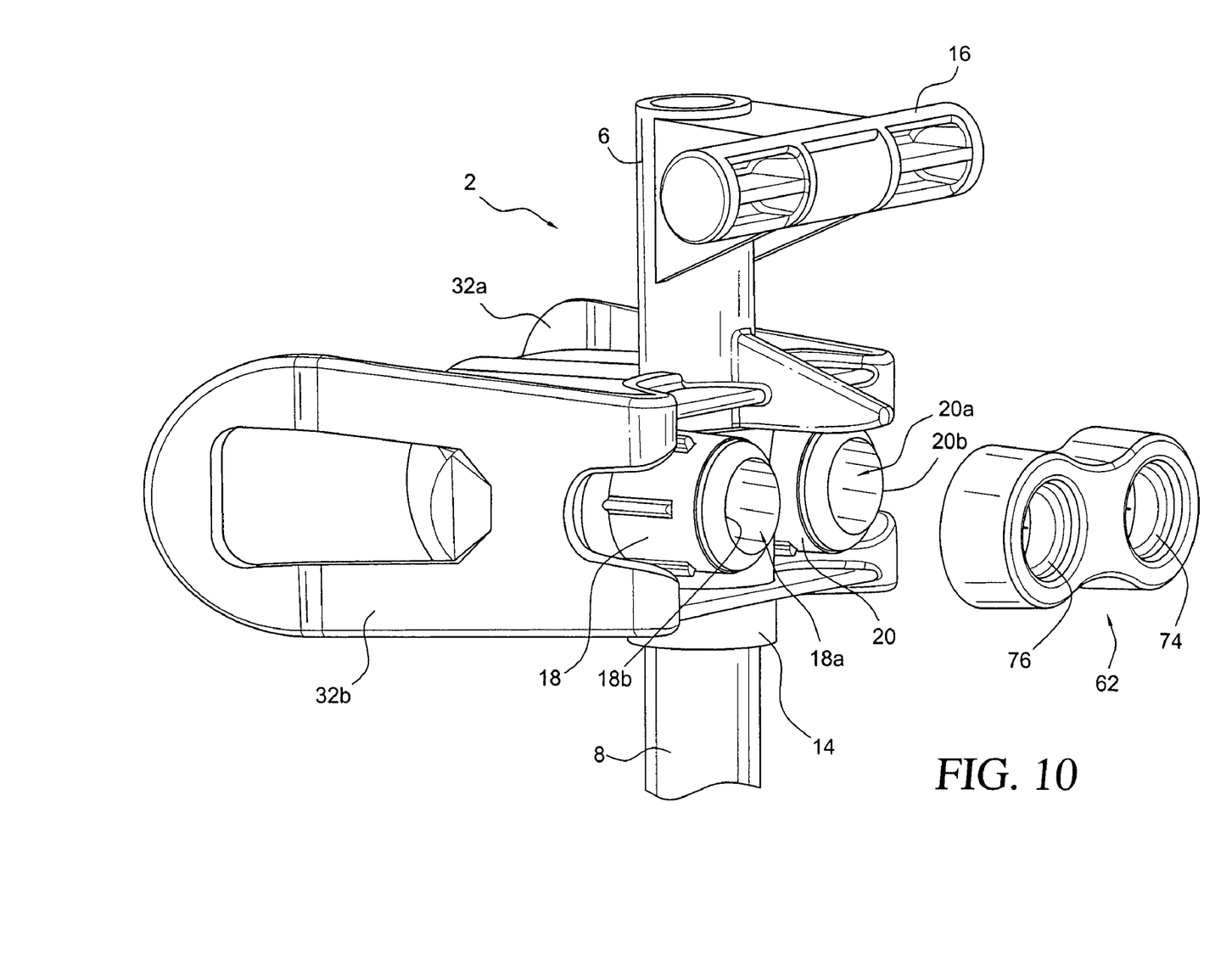
FIG. 10 shows the fitting of the instant invention with the assembled casing in alignment with the inlet and outlet of the fitting.
Figure 11:
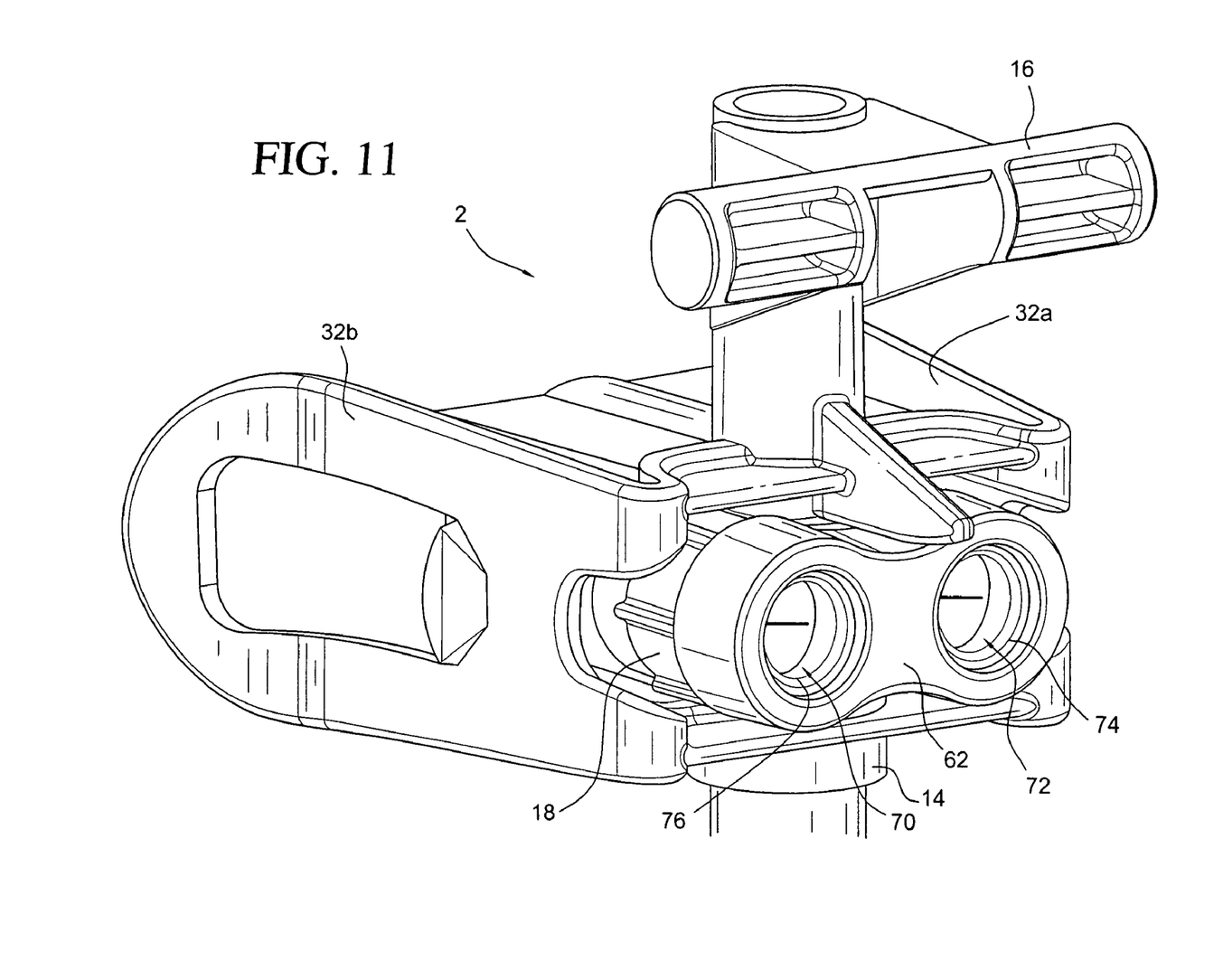
FIG. 11 shows a fitting of the instant invention having assembled thereto the casing of FIG. 9 for securing the sealing valve gaskets to the inlet and outlet of the fitting.

Another embodiment of the fitting of the instant invention is shown in FIGS. 8-11. There a different way in which valve gaskets are assembled onto the inlet and outlet of the fitting is illustrated. Insofar as most of the elements of the fitting shown in FIGS. 10 and 11 are functionally the same as those shown in FIGS. 4a and 4b, the same elements in the fitting of the alternative embodiment are designated with the same numbers.

FIG. 8 shows a cartridge or casing 62 that has a configuration in the form of a FIG. 8, with two bores or passages 64 and 66 formed internally from the back of the casing. The front wall or surface 68 of the casing, as best shown in FIG. 9, has openings 70 and 72 that are smaller than the openings at the back of the casing for the passages of bores 64 and 66. Two valve gaskets 74 and 76 are fitted into bores 64 and 66, respectively, when they are assembled in casing 62 per shown in FIG. 9. Given that the openings 70 and 72 at the front wall of casing 62 are smaller in diameter than the flanges 74d and 76d of gaskets 74 and 76, respectively, valve gaskets 74 and 76, when fully positioned in bores 64 and 66, are prevented from movement by the front wall of casing 62.

Valve gasket 74 and 76 shown in FIG. 8 are similar to the valve gaskets 28 and 30 shown in FIGS. 5a and 5b. Valve gaskets 74 and 76, like valve gaskets 28 and 30, may be made of silicone, rubber or some other elastomeric material. Instead of having multiple flaps, valve gaskets 74 and 76 each have a slit 74a and 76a, respectively, at the base of the gasket. As gaskets 74 and 76 are the same, only gaskets 76 is discussed below in detail. For the sake of simplicity, even though the duckbill and multi-flap types of valve gaskets may also be used with cartridge casing 62, the hereinbelow discussion focuses to the single slit type valve gaskets shown.

As illustrated, cup-shaped gasket 76 has a base portion having a closed end 76c with a slit 76a that can be pushed open by the output port 56 of the mount 4 when the fitting 2 is coupled thereto (FIG. 7A). Likewise, slit 74a of gasket 74 is pushed open by input port 58 of mount 4. The base portion further has a circumferential wall 76b that extends from closed end 76c to a circumferential lip flange 76d at the open end of gasket 76. Circumferential wall 76b of gasket 76 is dimensioned to sealingly form fit into bore 18a (FIG. 10) of inlet 18 while flange 76d is dimensioned to sealingly form fit into bore 66 of casing 62 when casing 62 is fitted to inlet 18 and outlet 20 of fitting 2. Once the base portion of gasket 76 is fully inserted into bore 18a, the back wall 76e of flange 76d rests on lip 18b of inlet 18 to form a tight seal with inlet 18. The back wall 74e of gasket 74 likewise rests on lip 20b of outlet 20 when circumferential wall 74b of gasket 74 is form fittedly inserted into bore 20a of outlet 29 and flange 74d sealingly form fits to bore 64 of casing 62, when casing 62 is assembled to the fitting, per shown by the assembled fitting 2 of FIG. 11. Once fully assembled to the inlet and outlet of fitting 2, casing 62 is bonded, either ultrasonically or by means of a solvent, to the fitting, so that casing 62 is fixedly retained to and could not be removed from fitting 2.

FIG. 10 is an exploded view showing casing 62 being positioned in alignment with inlet 18 and outlet 20 of fitting 2, with gasket 74 and 76 already assembled into the bores of casing 62. When casing 62 is fully assembled onto fitting 2, a fluid leak proof seal is effected at inlet 18 and outlet 20 of fitting 2, both when fitting 2 is coupled to mount 4 (per shown in FIG. 4) and when fitting 2 is not coupled to mount 4. Valve gaskets 74 and 76 prevent fluid from leaking out of fitting 2 when fitting 2 is not coupled to mount 4, and also prevent any fluid leak when inlet 18 and outlet 20 are mated to output port 56 (FIG. 7B) and input port 58, respectively, and fluid is passing between fitting 2 and mount 4.

With the alternative embodiment of the fitting as shown in FIGS. 10 and 11, by positioning the valve gaskets inside casing 62 and assembling the one piece casing 62 to the inlet and outlet of fitting 2, an easier and more efficient assembly process is achieved. Also, by using a one piece casing 62, the valve gaskets are assured to be retained at the inlet and outlet of the fitting, irrespective of whether or not fitting 2 is coupled to mount 4. Casing 62 in essence acts to hold the valve gaskets in place at the inlet and outlet of the fitting, so that the fitting may be readily coupled to and removed from the mount. As noted above, casing 62 may be made from the same material as fitting 2. For example, both the fitting and the casing may be made from PVC, or other similar plastics materials.

Instead of a single cartridge casing such as 62 shown in FIG. 8, each of the valve gaskets may be separately assembled into its individual cap or cartridge casing for attachment to its corresponding inlet/outlet. Each of the caps may also be solvent or ultrasonically bonded to the inlet/outlet to fixedly retain the respective valve gaskets to the inlet and the outlet of the fitting.

In as much as the present invention is subject to many variations, modifications and changes in detail, it is intended that all matters described throughout this specification and shown in the accompanying drawings be interpreted as illustrative only and not in a limiting sense. Accordingly, it is intended that the invention be limited only the spirit and scope of the hereto appended claims.

The invention claimed is:

1. A connector assembly, comprising:
    a fitting having
        a body including a proximal portion and a distal portion, two arms forming a crossbar provided at the proximal portion;
        an inlet and an outlet protruding from the distal portion;
        two wings extending in a direction opposite the direction to which said inlet and outlet protrude; and
    a mount to which said fitting couples having
        a longitudinal channel for accepting said body;
        a groove orthogonal to said channel onto which said crossbar rests when said body is positioned in said channel;
        an input port and an output port for mating with said outlet and said inlet, respectively, when said body is positioned in said channel.

2. Connector assembly of claim 1, wherein said fitting is connected to a heat exchanger, said heat exchanger having a tubing through which an infusate and circulating heated fluid for warming the infusate flow.

3. Connector assembly of claim 2, wherein said tubing comprises a distal port at a distal end of said tubing adapted to connect to a patient line whereto infusate input to said fitting and flown through said tubing is output.

4. Connector assembly of claim 2, wherein said tubing comprises multiple lumens, a central and an outer lumen effecting a continuous fluid path for a heated fluid surrounding a middle lumen wherethrough the infusate flows.

5. Connector assembly of claim 2, wherein said fitting is configured to have said inlet connected to a first lumen of said tubing and said outlet connected to a second lumen of said tubing, said fitting further is configured to have a proximal port adapted to accept the infusate and to establish a fluid path for the infusate to flow to a third lumen of said tubing.

6. Connector assembly of claim 1, wherein said fitting comprises a proximal port at the proximal end of said body adapted to connect to an infusate line to receive infusate.

7. Connector assembly of claim 1, wherein said mount is a part of a heater device whereat a fluid is heated to a predetermined temperature, the heated fluid output from said output port to said inlet of said fitting.

8. Connector assembly of claim 1, wherein said wings each have a first locking mechanism and wherein said mount comprises two sidewalls each positioned adjacent to a corresponding one of said wings, each of said side walls having a second locking mechanism so that when said body of said fitting is positioned in said channel of said mount, the first and second locking mechanisms for each pair of corresponding wing and sidewall coact to retain said body to said mount.

9. Connecter assembly of claim 8, wherein said fitting is removable from said mount when said pair of wings are compressed towards each other to unlock the first lock mechanisms at said wings from the second lock mechanisms at said mount.

10. Connector assembly of claim 1, wherein said fitting is coupled to said mount by having its cross bar rests on said groove with said body away from said mount so that the contact between said cross bar and said groove provides a pivot for said body to pivotally move into position in said channel with said inlet and outlet mated to said output port and input port, respectively.

11. Connector assembly of claim 1, wherein said inlet and outlet each are fitted with a valve gasket for mating to said output port and input port, respectively, to enable circulation of a heated fluid into and out of said fitting when the fluid is under pressure.

12. Connector assembly of claim 1, further comprising:
    a one piece casing having two passages each configured to accept a valve gasket, said casing adapted to be fixedly retained to said fitting with the valve gasket in each passage fitted to a corresponding one of said inlet and outlet, the passages of said outlet and inlet at said casing mating with said input and output ports, respectively, when said fitting is coupled to said mount, the valve gaskets in said passages preventing fluid leak from the inlet and outlet of said fitting when said fitting is not coupled to said mount and preventing fluid leak from the respective passageways established between said fitting and said mount by the mating of said inlet to said output port and said outlet to said input port.

13. A connector assembly, comprising a fitting connected to a heat exchanger having an elongate body, said body having a crossbar provided at its proximal portion and an inlet and an outlet protruding from its distal portion, two wings extending in a direction opposite the direction to which said inlet and outlet protrude; and a mount to which said fitting couples having a longitudinal channel for accepting said body, a groove orthogonal to said channel onto which said crossbar makes contact before said body is pivotally moved into position in said channel with said crossbar resting on said groove, an input port and an output port provided at said mount for mating with said outlet and said inlet, respectively, when said body is positioned in said channel.

14. Connector assembly of claim 13, wherein said heat exchanger comprises a tubing through which an infusate and circulating heated fluid for warming the infusate flow.

15. Connector assembly of claim 13, wherein said fitting further comprises a proximal port at the proximal end of said body adapted to connect to an infusate line to receive infusate to said fitting, the infusate flowing through a first lumen in said heat exchanger, the infusate being heated by a heated fluid circulating through other lumens in said heat exchanger, the infusate output from said heat exchanger to a patient line.

16. Connector assembly of claim 13, wherein said mount is a part of a heater device whereat a fluid is heated to a predetermined temperature, the heated fluid output from said output port to said inlet of said fitting for circulation in said heat exchanger and return to said heater via said outlet and said input port for reheating.

17. Connector assembly of claim 13, wherein said wings each have a first locking mechanism and wherein said mount comprises two sidewalls each positioned adjacent to a corresponding one of said wings, each of said side walls having a second locking mechanism so that when said body of said fitting is positioned in said channel of said mount, the first and second locking mechanisms for each pair of corresponding wing and sidewall coact to retain said body to said mount.

18. Connector assembly of claim 13, wherein said inlet and outlet each are fitted with a valve gasket for mating to said output port and input port, respectively, to enable circulation of a heated fluid into and out of said fitting when the fluid is under pressure.

19. Connector assembly of claim 13, further comprising:
a one piece casing having two passages each configured to accept a valve gasket, said casing adapted to be fixedly retained to said fitting with the valve gasket in each passage fitted to a corresponding one of said inlet and outlet, the passages of said outlet and inlet at said casing mating with said input and output ports, respectively, when said fitting is coupled to said mount, the valve gaskets in said passages preventing fluid leak from the inlet and outlet of said fitting when said fitting is not coupled to said mount and preventing fluid leak from the respective passageways established between said fitting and said mount by the mating of said inlet to said output port and said outlet to said input port.

20. Apparatus comprising:
a fitting having an elongate body, said body having a crossbar provided at its proximal portion and an inlet and an outlet protruding from its distal portion;
a mount to which said fitting couples having a longitudinal channel for accepting said body, a groove orthogonal to said channel onto which said crossbar makes contact before said body is pivotally moved into position in said channel with said crossbar resting on said groove, an input port and an output port for mating with said outlet and said inlet, respectively, when said body is positioned in said channel;
a heat exchanger connected to a distal end of said fitting, said heat exchanger having a plurality of lumens one of which connected to said inlet and other of which connected to said outlet, said one and other lumens fluidly connected at a distal end to establish a through fluid path therebetween; and
a heater to which said mount is a part of, said heater heating a fluid to a predetermined temperature, the heated fluid being output to said heat exchanger from the output port of said mount to said inlet of said fitting and flow from said one lumen to said other lumen and said outlet to be returned to said heater via said input port of said mount, the returned fluid being heated by said heater to the predetermined temperature.

21. Apparatus of claim 20, wherein said fitting has a proximal port to which an infusate line is connected to input infusate to said fitting, said fitting configured to connect the infusate line to a through lumen in said heat exchanger so that the infusate flows through said heat exchanger, the infusate being heated by the heated fluid as it flows along said through lumen.

22. Apparatus of claim 20, wherein said fitting includes two wings extending in a direction opposite the direction to which said inlet and outlet protrude, said wings each having a first locking mechanism, and wherein said mount comprises two sidewalls each positioned adjacent to a corresponding one of said wings, each of said side walls having a second locking mechanism so that when said body of said fitting is positioned in said channel of said mount, the first and second locking mechanisms for each pair of corresponding wing and sidewall coact to retain said body to said mount.

23. Apparatus of claim 20, wherein said inlet and outlet each are fitted with a valve gasket for mating to said output port and input port, respectively, to enable circulation of the heated fluid into and out of said fitting.

24. Apparatus of claim 20, further comprising:
a one piece casing having two passages each configured to accept a valve gasket, said casing adapted to be fixedly retained to said fitting with the valve gasket in each passage fitted to a corresponding one of said inlet and outlet, the passages of said outlet and inlet at said casing mating with said input and output ports, respectively, when said fitting is coupled to said mount, the valve gaskets in said passages preventing fluid leak from the inlet and outlet of said fitting when said fitting is not coupled to said mount and preventing fluid leak from the respective passageways established between said fitting and said mount by the mating of said inlet to said output port and said outlet to said input port.

* * * * *